United States Patent
Thimmaiah et al.

(10) Patent No.: US 11,419,803 B2
(45) Date of Patent: Aug. 23, 2022

(54) SKIN DARKENING COMPOSITION

(71) Applicant: Conopco, Inc., Englewood Cliffs, NJ (US)

(72) Inventors: Sreenivasa Thimmaiah, Kadur (IN); Ian Peter Stott, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 16/763,208

(22) PCT Filed: Nov. 2, 2018

(86) PCT No.: PCT/EP2018/079973
§ 371 (c)(1),
(2) Date: May 11, 2020

(87) PCT Pub. No.: WO2019/110212
PCT Pub. Date: Jun. 13, 2019

(65) Prior Publication Data
US 2020/0330349 A1 Oct. 22, 2020

(30) Foreign Application Priority Data
Dec. 6, 2017 (EP) .................................... 17205634

(51) Int. Cl.
*A61K 8/368* (2006.01)
*A61K 8/04* (2006.01)
*A61K 8/06* (2006.01)
*A61Q 19/04* (2006.01)

(52) U.S. Cl.
CPC .............. *A61K 8/368* (2013.01); *A61K 8/042* (2013.01); *A61K 8/06* (2013.01); *A61Q 19/04* (2013.01); *A61K 2800/31* (2013.01)

(58) Field of Classification Search
CPC .... A61K 8/368; A61K 2800/31; A61K 8/042; A61K 8/06; A61Q 19/04
See application file for complete search history.

(56) References Cited

U.S. PATENT DOCUMENTS

| | | | |
|---|---|---|---|
| 3,264,280 A | 8/1966 | Klaus et al. | |
| 4,683,244 A * | 7/1987 | Moeller | C07C 65/24 514/568 |
| 4,833,147 A * | 5/1989 | Moeller | A61K 8/368 514/263.31 |
| 8,338,364 B2 | 12/2012 | Hantash | |
| 10,093,698 B2 | 10/2018 | Chung et al. | |
| 2009/0053760 A1 | 2/2009 | Eggen et al. | |
| 2010/0104521 A1 | 4/2010 | Dal Farra et al. | |
| 2011/0312890 A1 | 12/2011 | Chandran | |
| 2012/0014885 A1 | 1/2012 | Collier | |
| 2015/0152139 A1 | 6/2015 | Hantash | |
| 2015/0274776 A1 | 10/2015 | Peschard et al. | |

FOREIGN PATENT DOCUMENTS

| | | |
|---|---|---|
| EP | 1604647 | 12/2005 |
| JP | 10081607 | 3/1998 |
| WO | WO9617589 | 6/1996 |
| WO | WO9956740 | 11/1999 |
| WO | WO2004062607 | 7/2004 |
| WO | WO2005079744 | 9/2005 |
| WO | WO2005099664 | 10/2005 |
| WO | WO2007129270 | 11/2007 |
| WO | WO2012112851 | 8/2012 |
| WO | WO2013063615 | 5/2013 |
| WO | WO2014080376 | 5/2014 |
| WO | WO2015081306 | 6/2015 |
| WO | WO2015174599 | 11/2015 |

OTHER PUBLICATIONS

Huang et al.,; Inhibition of the activity of mushroom tyrosinase by alkylbenzoic acids; Food Chemistry 2006; pp. 1-6; XP25129660; vol. 94; Elsevier.
Search Report and Written Opinion in EP17205634; dated Feb. 5, 2018.
Search report and Written Opinion in PCTEP2018079973; dated Jan. 15, 2019.
IPRP2 in PCTEP2018078916; Nov. 18, 2019.
Search Report and Written Opinion in PCTEP2018078916; dated Nov. 22, 2018; World Intellectual Property Org. (WIPO).
Search Report and Written Opinion in EP17201585; dated Feb. 6, 2018.
Yasunobu, K. et al.; Oxidation of Tyrosine-Containing; J. Biol. Chem.; 1959; 3291-3295; 234(12).
Schurink, M., et al.; Novel peptides with tyrosinase inhibitory activity; Peptides; 2007; pp. 485-495; 28(3).
Co-Pending Application, filed May 11, 2020, U.S. Appl. No. 16/763,207, Ganesh Chandramowli, et al.
Brenner, et al.; The Protective Role of Melanin Against UV Damage in Human Skin ; Photochem Photobiol.; 2007; pp. 539-549; 84(3).
"Seborrhoeic dermatitis", Wikipedia, https://en.wikipedia.org/wiki/Seborrhoeic_dermatitis, Retrieved Mar. 2, 2022; Mar. 2, 2022.
"Seborrheic Dermatitis_ What Is It, Diagnosis & Treatment", https://my.clevelandclinic.org/health/diseases/14403-seborrheic-dermatitis, Retrieved Mar. 2, 2022; Mar. 2, 2022.

\* cited by examiner

*Primary Examiner* — Jianfeng Song
(74) *Attorney, Agent, or Firm* — Gerard J. McGowan, Jr.

(57) ABSTRACT

The invention relates to a composition and a method of darkening human skin. The composition comprises select alkyl or alkyloxy benzoic acids.

9 Claims, No Drawings

SKIN DARKENING COMPOSITION

FIELD OF THE INVENTION

The invention relates to a composition and a method of darkening human skin.

BACKGROUND OF THE INVENTION

Most people are concerned with certain characteristics of their skin. For example, consumers with age spots or freckles often wish that such pigmented spots be less pronounced. Some others may wish to address darkening of skin caused by exposure to sunlight or alternatively may wish to lighten their natural skin color. These needs of consumers led to the development of products that reduce or delay the production of melanin in melanocytes (i.e. reduce melanogenesis).

On the other hand, there are people who desire darker skin tone or a tanned look.

The melanocytes transfer melanin to the keratinocyces which are in their vicinity where it (melanin) serves to protect cellular DNA from UV-induced damage by virtue of its ability to absorb UV-radiation. When the skin is exposed to UV light, the synthesis of melanin increases as does the transfer of melanin to the keratinocytes. This results in visible darkening of the skin color, which is known as a tan. Tanning due to over exposure to UV radiation is a known phenomenon. However, it is also known that such exposure to UV radiation causes accelerated aging which may lead to increased incidences of skin cancer.

Melanin is the black pigment present in our hair and skin and is synthesized by melanosomes from tyrosine. Melanosomes are organelles found in melanocytes, a cell type present at dermis-epidermis junction. Tyrosine is acted upon by an enzyme, tyrosinase, which is the key step in melanogenesis.

In the melanosomes, the melanin is synthesized from monomers and is transferred to the neighboring cells called keratinocytes. The keratinocytes divide and differentiate and thus transport the melanosome to the surface of the skin. The shade or hue of the colour of our skin depends on the number and the size of melanocytes, the melanin content and the rate of formation and migration/transfer of melanosomes to keratinocytes.

Incidence of melanoma in caucasians is more due to lack of melanin in their skin. UV easily penetrates and induce cellular changes and result in skin cancer. To avoid this, people use various methods like chemicals agents, or controlled UV treatment to get tanned. These chemicals may be harsh and they act by depositing on the skin followed by themselves turning in to melanin like color. They have the disadvantage of being washed off once they come in contact with water. In fact, some of these chemicals turn yellow rather than brown; while some of them do not afford a pleasant sensory. Controlled UV exposure could also be a problem because it is difficult to calculate the desired dose, which varies from individual to individual.

Hence, there is a need to come up with solutions to increase skin's melanin naturally. The present inventors have solved this problem by coming up with molecules which induce melanin in natural way i.e. through stimulating the melanin synthesis machinery to synthesis more melanin. This extra melanin synthesized can protect the skin by absorbing UV radiation.

There are some actives which are known and have been used to affect pigmentation of skin, even without exposure to UV rays or sun rays. Such actives are known as sunless tanning agents. Dihydroxyacetone is one such sunless tanning agent which has been extensively used. However, DHA has certain negative connotations in consumer's minds and so there is a need for developing new and potentially safer actives that are highly effective. In this respect, the present inventors experimented extensively with a large number of actives presently being used in skin care products for different purposes and hit upon very specific benzoic acid derivatives that act as skin darkening agents.

Huang, X.-H. et al., Inhibition of the activity of mushroom tyrosinase by alkylbenzoic acids. *Food Chem.* 94 (2006), pp. 1-6. In this paper, certain benzoic acid derivatives have been implicated as mushroom tyrosinase inhibitors for lightening skin, anti-browning benefit for fruits, vegetables and other frozen foods. This is in direct contrast to the findings of the present invention where a more direct methodology involving human primary melanocytes was used and it has been inferred that certain very specific (C7 to C12) alkyl and alkyloxy benzoic acids exhibit skin darkening.

WO9617589 (Kao) discloses a method of stimulating collagen synthesis and of smoothing or removing wrinkles, which comprise administering an effective amount of a benzoic acid derivative or a salt thereof, and use of this compound for agents for stimulating synthesis of collagen, and smoothing or removing wrinkles. This compound stimulates collagen synthesis in human dermal fibroblasts and consequently smooths or removes wrinkles caused by aging and/or photoaging. There is no indication in this patent publication that these actives can cause skin darkening.

It is thus an object of the present invention to provide for a skin darkening composition whose activity is enabled through use of widely used and safe actives.

SUMMARY OF THE INVENTION

The present invention relates to a method of darkening skin comprising the step of applying a composition comprising (i) a compound of the formula 1

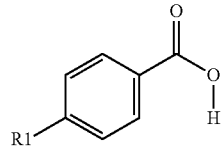

Wherein R1 is R2 or OR2
Wherein R2 is a C7 to C12 alkyl group; and
(ii) a cosmetically acceptable vehicle.

According to another aspect there is provided use of the composition as hereinbefore disclosed for darkening skin.

Yet another aspect provides for use of a compound of the formula 1 in the manufacture of a composition to provide skin darkening.

DETAILED DESCRIPTION OF THE INVENTION

These and other aspects, features and advantages will become apparent to those of ordinary skill in the art from a reading of the following detailed description and the appended claims. For the avoidance of doubt, any feature of one aspect of the present invention may be utilised in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description indicating amounts of material or conditions of reaction, physical properties of materials and/or use are to be understood as modified by the word "about".

Numerical ranges expressed in the format "from x to y" are understood to include x and y. When for a specific feature multiple preferred ranges are described in the format "from x to y", it is understood that all ranges combining the different end points are also contemplated.

As used herein the term "comprising" encompasses the terms "consisting essentially of" and "consisting of". Where the term "comprising" is used, the listed steps or options need not be exhaustive. Unless otherwise specified, numerical ranges expressed in the format "from x to y" are understood to include x and y. In specifying any range of values or amounts, any upper value or amount can be associated with any particular lower value or amount. Except in the examples and comparative experiments, or where otherwise explicitly indicated, all numbers are to be understood as modified by the word "about". All percentages and ratios contained herein are calculated by weight unless otherwise indicated. As used herein, the indefinite article "a" or "an" and its corresponding definite article "the" means at least one, or one or more, unless specified otherwise. The various features of the present invention referred to in individual sections above apply, as appropriate, to other sections mutatis mutandis. Consequently, features specified in one section may be combined with features specified in other sections as appropriate. Any section headings are added for convenience only, and are not intended to limit the disclosure in any way.

By 'A skin darkening composition' as used herein, is meant to include a composition for topical application to any keratinous substrate of mammals, especially humans. Such a composition could be of the leave-on or of the wash-off/rinse-off type. By a leave-on composition is meant a composition that is applied to the desired skin surface and left on for a period of time (say from one minute to 24 hours) after which it may be wiped or rinsed off with water, usually during the regular course of personal washing. By a wash-off/rinse off composition is meant a composition that is applied to the desired skin surface for a shorter period of time say of the order of seconds or minutes and usually contains sufficient surfactants that aids in cleaning the surface which may be rinsed off with copious amounts of water. It is particularly preferred that the composition of the invention is formulated as a leave-on formulation. The composition may also be formulated into a product which is applied to a human body for improving the appearance, cleansing, odor control or general aesthetics. The composition of the present invention can be in the form of a liquid, lotion, cream, foam, scrub, gel or stick form and may be delivered through a roll-on device or using a propellant containing aerosol can. "Skin" as used herein is meant to include skin on any part of the body e.g., neck, chest, back, arms, underarms, hands, legs, buttocks and scalp. It also includes keratinous fibers like hair which could be darkened using the composition of the invention.

Melanin is produced due to a complex set of reactions within the melanocytes involving, at a basic level, the enzyme tyrosinase and the amino acid L-tyrosine. It is known that tyrosinase is an essential component of melanin synthesis. Tyrosinase catalyzes conversion of L-tyrosine to dopaquinone via L-DOPA (L-3,4-dihydroxyphenylalanine) as an intermediate. Dopaquinone undergoes further conversion to form melanin.

An increase in the amount of the biological pigment 'melanin' in the melanocytes is usually associated with cytotoxicity and uncontrolled proliferation. Some known agents are not as safe as they should be and examples include forskolin and IBMX (3-isobutyl-1-methylxanthine) Sunless tanning agents are formulated into two types of cosmetic products. Of these, the most traditional is the self-tanning lotion. The imparted benefit is to achieve a skin coloration equivalent to that achieved by from basking in the sun. More recently, a second product category has arrived. Therein a sunless tanning agent in small amounts is added to a typical moisturizing lotion.

Most prominent among the sunless tanning agents is dihydroxyacetone ("DHA" which chemically is 1,3-dihydroxy-2-propanone). DHA is believed to exert its effect through interactions between its hydroxyl groups and the amino groups of amino acids and peptides naturally occurring in the hydrolipid pellicle and first layers of the stratum corneum of the skin. These Maillard reactions are believed (see, e.g., Bobin et al., J. Soc. Cosmet. Chem. 35: 255 (1984)) to lead to formation of brown pigments in the skin, thereby giving it an appearance like that of a naturally obtained tan.

We have now determined that some selective class of benzoic acid derivatives which are known to have antimicrobial properties and used as preservatives also provide for skin darkening. This has been verified in a cell based assay which is more representative of in vivo action as compared to mushroom tyrosinase based assays which have been used so far in screening of skin colouration/lightening actives.

Disclosed in accordance with the invention is a skin darkening composition comprising (i) a compound of the formula 1

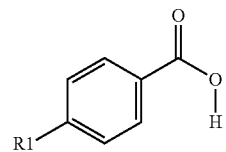

Wherein R1 is R2 or OR2

Wherein R2 is a C7 to C12 alkyl group; and (ii) a cosmetically acceptable vehicle.

The preferred compounds of the formula 1 for inclusion in the composition of the invention are selected from one or more of 4-heptyl benzoic acid, 4-heptyloxybenzoic acid, 4-octyloxybenzoic acid, 4-nonyloxybenzoic acid, 4-undecyloxybenzoic acid, or 4-decyloxybenzoic acid. Particularly preferred compounds of formula 1 are selected from one or more of 4-heptyloxybenzoic acid, 4-octyloxybenzoic acid, 4-nonyloxybenzoic acid, and 4-undecyloxybenzoic acid.

The compounds referred to above have the structures as shown below:

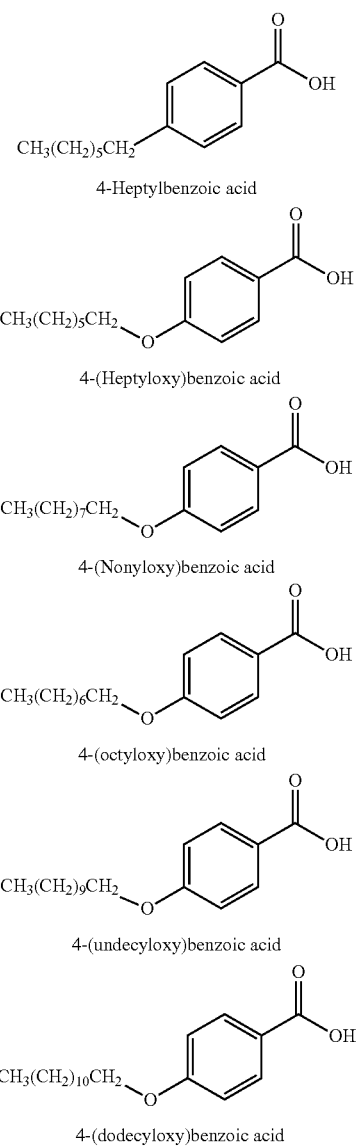

It has been observed that the compounds as claimed are effective in melanin production while other compounds of the alkyl or alkyloxy benzoic acid are ineffective in producing this effect. The present inventors tested alkyl and alkyloxy chains below C7 i.e C1 to C6 and also alkyl and alkyloxy chains above C12 and found them to be relatively ineffective for the present benefit. Further, the present invention has been found to be limited to the alkyl or alkyl oxy branching at the 4 position and does not work when these groups are linked at any other position on the benzene ring.

It has been observed that the compounds of the formula (I) are effective at concentrations of 1 to 50 μmolar, preferably from 5 to 35 μmolar concentration under in vitro conditions. This observation indicates that the molecules are likely to be efficacious at low dosage in cosmetic compositions, e.g., sunless tanning compositions. Without wishing to be bound by theory, the present inventors believe that the benzoic acid derivatives at the para position (C7-C12 alkyl or alkyloxy derivaized) induces melanin synthesis in human primary melanocytes via cellular signaling not acting as substrate or directly altering enzyme activity per se. They induce melanin synthesis at cellular level and may be acting on cellular signaling.

It has been further observed that in accordance with this invention, cellular melanin synthesis ranges from 110 to 150% of that of a control sample. This is a significant increase comparable to increase usually brought about by standard/known ingredients.

Usually such compounds are associated with cytotoxicity which is an unavoidable side effect. However, it has been observed that preferably the cell viability in the present invention is more than 75%, in more preferred cases more than 90% and in most preferred cases more than 95%. In other words, the cytotoxicity of the molecules of the formula (I) is less than 25%, preferably less than 10% and most preferably less than 5%. These numbers are under in vitro conditions.

It is preferred that the compound of formula 1 in the composition of the invention is included in 0.01 to 10%, preferably 0.05 to 5%, more preferably 0.1 to 3% by weight of the composition.

The composition comprises a cosmetically acceptable vehicle which is preferably selected from an anhydrous base, a gel, lotion, cream or emulsion. When the composition in accordance with the invention is a cosmetic composition as above, it preferably comprises one or more of fragrance, surfactant, organic sunscreen, inorganic sunscreen, extender pigment and preservative.

Sunscreens include those materials which block harmful ultraviolet light. Preferred sunscreens are the derivatives of p-aminobenzoic acid (PABA), cinnamate and salicylate. For example, avobenzophenone (Parsol® 1789), octyl methoxycinnamate and 2-hydroxy-4-methoxy benzophenone (also known as oxybenzone) can be used. Octyl methoxycinnamate and 2-hydroxy-4-methoxy benzophenone are commercially available under the trade marks, Parsol® MCX and Benzophenone-3, respectively. Ecamsule®, a benzylidene camphor derivative, and drometrizole trisiloxane, a benzotriazole, may also be used. Further examples include Octocrylene, phenylbenzimidazole sulfonic acid (also known as Ensulizole®), ethylhexyl salicylate, diethylhexyl naphthylate, bimotrizinole (trade marked as Tinosorb® S) and bisoctrizole (Tinosorb® M). Inorganic sunscreens include oxides like titanium dioxide and zinc oxide which reflect or scatter the sunrays. The quantity of sunscreens present in the compositions could vary depending upon the degree of protection desired from UV radiation. Preferably, the compositions comprise 0.01 to 15% by weight, more preferably 0.1 to 10 and most preferably 0.5 to 7.5% by weight sunscreen.

Illustrative examples of the types of fragrances that may be used include those comprising terpenes and terpene derivatives like those described in Bauer, K., et al., Common Fragrance and Flavor Materials, VCH Publishers (1990). Further examples include myrcene, dihydromyrenol, citral, tagetone, cis-geranic acid, citronellic acid, mixtures thereof.

The carrier acts as diluent or dispersant for the ingredients of the compositions. The carrier may be aqueous-based, anhydrous or an emulsion, whereby a water-in-oil or oil-in-water emulsion is generally preferred. If the use of water is desired, water typically makes up the balance of the composition, which most preferably is from 40 to 80% by weight of the composition.

In addition to water, organic solvents may optionally be included as carrier to assist any other carrier in the compositions of the present invention. Examples include alkanols like ethyl and isopropyl alcohol.

Other suitable organic solvents include ester oils like isopropyl myristate, cetyl myristate, 2-octyldodecyl myristate, avocado oil, almond oil, olive oil and neopentylglycol dicaprate. Typically, such ester oils assist in emulsifying the compositions, and an effective amount is often used to yield a stable, and most preferably, water-in-oil emulsion.

Emollients may also be used, if desired, as a carrier. Alcohols like 1-hexadecanol (i.e. cetyl alcohol) are preferred. Other emollients include silicone oils and synthetic esters. Silicone oils suitable for use include cyclic or linear polydimethylsiloxanes containing from 3 to 9, preferably from 4 to 5 silicon atoms. Non-volatile silicone oils useful as emollients include polyalkyl siloxanes, polyalkylaryl siloxanes and polyether siloxane copolymers. The non-volatile polyalkyl siloxanes useful polydimethylsiloxanes. Silicone elastomers may also be used. The ester emollients that may optionally be used are:

(i) alkenyl or alkyl esters of fatty acids having 10 to 20 carbon atoms. Examples thereof include isoarachidyl neopentanoate, isononyl isonanonoate, oleyl myristate, oleyl stearate, and oleyl oleate;
(ii) ether-esters such as fatty acid esters of ethoxylated fatty alcohols;
(iii) polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters;
(iv) wax esters such as beeswax, spermaceti, stearyl stearate and arachidyl behenate; and,
(v) sterols esters, of which cholesterol fatty acid esters are examples.

Emollients, when present, typically make up from 0.1 to 50% by weight of the composition, including all ranges subsumed therein.

Fatty acids having from 10 to 30 carbon atoms may also be included as carriers. Examples of such fatty acids include pelargonic, lauric, myristic, palmitic, stearic, isostearic, oleic, linoleic, arachidic, behenic or erucic acid and mixtures thereof.

Humectants of the polyhydric alcohol type may also be employed in the compositions. The humectant often aids in increasing the effectiveness of the emollient, reduces scaling at the skin surface, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results, the humectant is preferably propylene glycol or sodium hyaluronate. Other humectants which may be used include hydroxyethyl urea. The amount of humectant may be 0.2 to 25% by weight and preferably from 0.5 to 15% by weight of the composition.

Moisturisation may be improved through use of petrolatum or paraffin. Thickeners may also be utilized as a portion of the carrier in the compositions. Typical thickeners include cross-linked acrylates (e.g. Carbopol® 982), hydrophobically-modified acrylates (e.g. Carbopol® 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Amounts of the thickener may range from 0.001 to 5, optimally from 0.01 to 0.5% by weight of the composition.

Surfactants may also be present. When present, the total amount of surfactants is 2 to 40% by weight, and preferably from 4 to 20% by weight, optimally from 5 to 12% by weight of the composition. The surfactant is selected from the group consisting of anionic, nonionic, cationic and amphoteric actives. Particularly preferred nonionic surfactants are those with a $C_{10-20}$ fatty alcohol or acid hydrophobe condensed with from 2 to 100 moles of ethylene oxide or propylene oxide per mole of hydrophobe; mono- and di-fatty acid esters of ethylene glycol; fatty acid monoglyceride; sorbitan, mono- and di-C8-C20 fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_{8\ to\ 20}$ acyl isethionates, acyl glutamates, $C_{8\ to\ 20}$ alkyl ether phosphates and combinations thereof.

Various other ingredients may also be used in compositions. Actives are defined as skin benefit agents other than emollients and other than ingredients that merely improve the physical characteristics of the composition. Although not limited to this category, general examples include extender pigments such as talcs and silicas, as well as alpha-hydroxy acids, beta-hydroxy acids and zinc salts.

Beta-hydroxy acids include salicylic acid. Zinc oxide and zinc pyrithione are examples of useful zinc salts.

Compositions, especially those containing water, need to be protected against harmful microorganisms. Anti-microbial compounds, such as triclosan, and preservatives may become necessary. Suitable preservatives include alkyl esters of p-hydroxybenzoic acid, hydantoin derivatives, propionate salts, and a variety of quaternary ammonium compounds. Particularly preferred preservatives are methyl paraben, propyl paraben, phenoxyethanol and benzyl alcohol. Preservatives are from 0.1 to 2% by weight of the composition.

The packaging could be a patch, bottle, tube, roll-ball applicator, propellant driven aerosol device, squeeze container or lidded jar.

The invention provides for a method of darkening skin comprising the step of applying a composition as hereinbefore disclosed on to the desired skin surface. The method is preferably non-therapeutic in nature. The suitable skin surface includes facial skin, hands and arms, feet and legs and neck and chest. Of interest is facial skin including the forehead, perioral, chin, periorbital, nose, and/or cheeks. The composition may be applied and left on the desired surface for a sufficient time or may be applied repeatedly a sufficient number of times. In certain embodiments, the contact time is greater than about 1 hour, 2 hours, 6 hours, 8 hours, 12 hours, or 24 hours. The contact time is the time from application of the composition until the composition is removed. In certain embodiments, the composition may be removed by rinsing or washing the substrate. The composition may be removed by washing or rinsing the skin. The composition may be applied at least once daily. In other embodiments, the composition is applied at least twice daily. Multiple applications may occur over the course of at least about one week. Alternately, the application period may last more than about 4 weeks or more than about 8 weeks. In certain embodiments, the treatment period will extend over multiple months (i.e., 3 to 12 months) or years. In the case of cosmetic composition, the composition may be applied daily for prolonged period.

According to yet another aspect the invention provides for use of the composition as hereinbefore disclosed for darkening skin. The use is preferably cosmetic. The invention also provides for use of the compound of formula 1 in the manufacture of a composition to provide skin darkening.

The invention will be explained in detail with the help of the following non-limiting examples.

EXAMPLES

All test compounds were purchased from SIGMA-ALDRICH as powders. They were tested at various concentrations in cell culture (see below). Forskolin (SIGMA Cat. # F6886) was used as reference comparators, as they have been reported to increase melanin content. Neonatal foreskin primary human epidermal melanocytes were procured from Cascade Biologicals (labelled passage P0). Melanocytes were maintained in Medium 254CF (Cascade Cat. # M-254CF-500) supplemented with human melanocyte growth supplement (Cascade; Cat. # S-002-5), hereafter referred to as MGM. Cells were maintained at 37° C. in a humidified incubator with 5% $CO_2$ atmosphere.

Cell Viability and Melanin-Content Assay 50,000 cells were seeded in 24 well plate in MGM; after 24 hours, cultures were treated with various concentrations of the test materials and left undisturbed for a further period of 72 hours. Comparative vehicle controls of 0.25% (v/v) DMSO were also set up in parallel, simultaneously. At the end of the incubation period, cell viability was determined using the calcein method.

Briefly, cell culture spent media was removed and cells washed once with 0.4 ml of 1× PBS-Ca—Mg solution. Fresh 1 μM calcein-AM was added (0.2 ml/well), including to control wells without cells. Plates were covered with aluminium foil and incubated for 30 minutes. at 37° C. in the regular $CO_2$ incubator. Calcein fluorescence was then measured (λmax 490 nm and λmax 520 nm) in TECAN® M1000 Infinite series plate reader.

Melanin Content Assay

After calcein fluorescence readings were obtained, cells were drained and added fresh 125 μl of 1N NaOH (in 10% DMSO) per well. Cells were lysed by resuspension and incubation (60° C./1 hour.). Then this lysate was transferred to a fresh 386-well plate and measured OD405 nm in a TECAN M1000 plate reader (estimate of relative melanin content).

Calculations

Calcein fluorescence values were ratio converted in 0 to 100 scale (% viability), with 100 representing the value of the 0.25% DMSO sample. % Melanin content was calculated as the ratio between $OD_{405\,nm}$ value of any sample to that of DMSO reference sample.

Normalized melanin content value was then calculated as 100*(% Melanin Content)/(% Cellular viability).

The percentage Increase in melanin content was estimated as [(Normalized melanin content)–100]

The following six molecules were tested:

Example 1: 4-heptyl benzoic acid
Example 2: 4-heptyloxybenzoic acid
Example 3: 4-octyloxybenzoic acid
Example 4: 4-nonyloxybenzoic acid
Example 5: 4-undecyloxybenzoic acid
Example 6: 4-decyloxybenzoic acid The data on % viability of the various compounds tested at many concentrations along with the % melanin content as compared to vehicle control is summarised in the table below.

| Material Tested | Concentration, micromolar | % Viability | % Melanin content |
|---|---|---|---|
| control |  | 100 | 100 |
| Example 1 | 25 | 93 | 113 |
| Example 1 | 12.5 | 102 | 129 |
| Example 1 | 6.25 | 102 | 124 |
| Example 2 | 25 | 96 | 137 |
| Example 2 | 20 | 95 | 129 |
| Example 2 | 15 | 96 | 126 |
| Example 2 | 10 | 94 | 117 |
| Example 3 | 25 | 86 | 86 |
| Example 3 | 20 | 100 | 127 |
| Example 3 | 15 | 103 | 144 |
| Example 3 | 10 | 101 | 127 |
| Example 4 | 25 | 103 | 137 |
| Example 4 | 20 | 103 | 130 |
| Example 4 | 15 | 109 | 136 |
| Example 4 | 10 | 109 | 129 |
| Example 4 | 5 | 102 | 126 |
| Example 5 | 25 | 79 | 120 |
| Example 5 | 20 | 90 | 134 |
| Example 5 | 15 | 100 | 146 |
| Example 5 | 10 | 97 | 136 |
| Example 6 | 25 | 76 | 93 |
| Example 6 | 20 | 82 | 101 |
| Example 6 | 15 | 100 | 122 |
| Example 6 | 10 | 102 | 129 |
| Example 6 | 5 | 104 | 126 |

The data in the Table above indicates that the compounds as per the invention (Example 1 to 6) provide for increase in melanin content as compared to control.

The cell viability for all of the samples at the concentrations tested is also quite good as is evident from the % viability that is within acceptable limits.

The invention claimed is:

1. A method of darkening skin comprising the step of applying a composition comprising
   (i) from 5-25 micromolar concentration of a compound of the formula 1

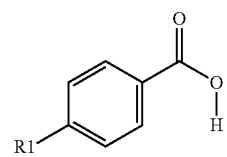

Wherein R1 is R2 or OR2
Wherein R2 is a C7 to C12 alkyl group; and (ii) a cosmetically acceptable vehicle
on to a desired skin surface; wherein cellular melanin synthesis ranges from 110 to 150% of that of a control sample.

2. The method as claimed in claim 1 wherein the compound of formula 1 is selected from 4-heptyl benzoic acid, 4-heptyloxybenzoic acid, 4-octyloxybenzoic acid, 4-nonyloxybenzoic acid, 4-undecyloxybenzoic acid, or 4-decyloxybenzoic acid.

3. The method as claimed in claim 2 wherein the compound of formula 1 is selected from 4-heptyloxybenzoic acid, 4-octyloxybenzoic acid, 4-nonyloxybenzoic acid, and 4-undecyloxybenzoic acid.

4. The method as claimed in claim 1 wherein the cosmetically acceptable vehicle is selected from an anhydrous base, a gel, lotion, cream or emulsion.

5. The method as claimed in claim 1 wherein said method is non-therapeutic in nature.

6. The method of claim 1 wherein the desired skin surface is the facial skin.

7. The method of claim 1 wherein the desired skin surface is the hand.

8. The method of claim 1 wherein the desired skin surface is the feet.

9. The method of claim 6 wherein the facial skin is the chin.

* * * * *